(12) United States Patent
Rathjen

(10) Patent No.: US 10,660,795 B2
(45) Date of Patent: May 26, 2020

(54) OPHTHALMOLOGICAL PATIENT INTERFACE APPARATUS

(71) Applicant: Ziemer Ophthalmic Systems AG, Port (CH)

(72) Inventor: Christian Rathjen, Bremen (DE)

(73) Assignee: Ziemer Ophthalmic Systems AG, Port (CH)

( * ) Notice: Subject to any disclaimer, the term of this patent is extended or adjusted under 35 U.S.C. 154(b) by 168 days.

(21) Appl. No.: 15/832,219

(22) Filed: Dec. 5, 2017

(65) Prior Publication Data

US 2018/0153740 A1     Jun. 7, 2018

(30) Foreign Application Priority Data

Dec. 5, 2016     (EP) .................................... 16020480

(51) Int. Cl.
| | |
|---|---|
| A61F 9/009 | (2006.01) |
| A61B 3/10 | (2006.01) |
| A61B 3/00 | (2006.01) |
| A61F 9/008 | (2006.01) |

(52) U.S. Cl.
CPC ............ *A61F 9/009* (2013.01); *A61B 3/0025* (2013.01); *A61B 3/0058* (2013.01); *A61B 3/102* (2013.01); *A61F 9/008* (2013.01); *A61F 9/00814* (2013.01); *A61F 2009/00872* (2013.01); *A61F 2009/00897* (2013.01)

(58) Field of Classification Search
CPC .. A61F 9/009; A61F 9/00825; A61F 9/00831; A61F 9/00836; A61F 2009/00865; A61F 2009/0087; A61F 2009/00872; A61F 2009/00893; A61F 2009/00897; F04C 2270/041
USPC .......................................................... 606/4
See application file for complete search history.

(56) References Cited

U.S. PATENT DOCUMENTS

2013/0226160 A1 *     8/2013     Rathjen ............... A61F 9/00825
                                                                   606/4

FOREIGN PATENT DOCUMENTS

WO          2013053367 A1          4/2013

\* cited by examiner

*Primary Examiner* — Jon Eric C Morales
(74) *Attorney, Agent, or Firm* — Banner & Witcoff, Ltd.

(57) ABSTRACT

An ophthalmological patient interface apparatus (4), having a coupling apparatus (41) for mechanically coupling to an application head (3) of an ophthalmological laser system (10), comprises a lens-element system (44) which is arranged between the eye (2) and the application head (3) in the state coupled to the application head (3) during the treatment of an eye (2), said lens-element system being coupled into the beam path from the projection lens (30) to the eye (2). The lens-element system (44) is configured to image a first focal area (B) of the projection lens (30) disposed upstream of the lens-element system (44) in the beam path onto a second focal area (B*) in the eye (2) disposed downstream of the lens-element system (44) in the beam path, in such a way that a laser beam (L) focussed onto the first focal area (B) by the projection lens (30) causes tissue processing in the second focal area (B*) in the eye (2).

20 Claims, 3 Drawing Sheets

OPHTHALMOLOGICAL PATIENT INTERFACE APPARATUS

This application claims priority to and the benefit of European Patent Application No. 16020480.6 filed on Dec. 5, 2016. The above identified is incorporated by reference herein in its entirety.

TECHNICAL FIELD

The present invention relates to an ophthalmological patient interface apparatus and an ophthalmological laser system having an ophthalmological patient interface apparatus. In particular, the present invention relates to an ophthalmological patient interface apparatus having a fastening apparatus, for fastening the patient interface apparatus to an eye of a patient, and a coupling apparatus for mechanically coupling the patient interface apparatus to an application head of an ophthalmological laser system.

PRIOR ART

Currently, the treatment of eye tissue, for example for tissue incisions and tissue removal, is typically carried out using laser technology. For tissue processing, in particular, use is made of strongly focussed femtosecond laser pulses which have typical pulse widths of 100 fs to 1000 fs (1 $fs=10^{-15}$ s). Currently, commercial femtosecond laser systems are used to treat the cornea of the eye, in particular to undertake refractive corrections on the cornea. However, since other tissue parts and tissue regions of the eye, e.g. sclera, lens and retina, also can be treated with the laser pulses, different working distances and hence different focal distances are required for the various fields of application. In order to obtain different application-specific focal diameters, focal shapes, focal extents in the projection direction and/or beam divergences, it is likewise necessary to use different projection optical units with a different numerical aperture (NA) in each case. In general, a high NA is desirable because small foci (spot dimensions) and hence a smaller incision zone per pulse can be produced with a high NA. In the case of the use on the eye with a short working distance, a weight that is as low as possible and a small installation size of the projection optical unit are to be sought after.

However, on account of the desired small installation size, high NA, short working distances and very small focal dimensions (spot dimensions), it is hardly possible to produce projection lenses with so-called zoom lenses which can cover a large working range, in particular the whole eye. If the working distance of the projection lenses were to be increased, it would be easier to design zoom lenses with large working ranges, but the outlay in terms of costs, installation space and weight increases overproportionally with working distance, focusing strength and depth region, and so such systems are no longer justifiable from an economic point of view and the suitability for use is significantly restricted.

WO 2013/053367 describes a laser treatment apparatus and interface apparatuses which can be coupled in a removable manner to the laser treatment apparatus. Each of the interface apparatuses comprises a transparent contact body with an abutment area to be placed onto the eye. The interface apparatuses have different optical properties and change the spatial orientation of the beam focus of the laser treatment apparatus with respect to the abutment area. Expressed differently, the interface apparatuses according to WO 2013/053367 displace the focus of the laser treatment apparatus such that the latter comes to rest in a different region of the eye in a manner specific to the application. The interface apparatuses according to WO 2013/053367 are not suitable for laser treatment systems with projection lenses that carry out mechanical scanning movements during the treatment since the interface apparatuses would have to be moved along with the projection lens for maintaining unchanging imaging properties (in particular the spot dimensions) and would injure the eye contacting the abutment area in the process.

SUMMARY OF THE INVENTION

It is an object of the present invention to propose an ophthalmological patient interface apparatus and an ophthalmological laser system having an ophthalmological patient interface apparatus, which do not have at least some of the disadvantages of the prior art. In particular, it is an object of the present invention to propose an ophthalmological patient interface apparatus and an ophthalmological laser system having an ophthalmological patient interface apparatus which facilitate different treatment depths in the eye without having to displace the focus of the ophthalmological laser system therefor.

According to the present invention, these objects are achieved by the features of the independent claims. Further advantageous embodiments moreover emerge from the dependent claims and the description.

The aforementioned objects are achieved by the present invention by virtue of, in particular, an ophthalmological patient interface apparatus, which comprises a coupling apparatus for mechanically coupling the patient interface apparatus to an application head of an ophthalmological laser system, moreover comprising a lens-element system which is arranged between the eye and the application head in the state where the patient interface apparatus is coupled to the application head during the treatment of an eye, said lens-element system being coupled into a beam path from a projection lens of the application head to the eye. Here, the lens-element system is configured in such a way that it images a first focal area of the projection lens disposed upstream of the lens-element system in the beam path onto a second focal area in the eye disposed downstream of the lens-element system in the beam path, in such a way that a laser beam focussed onto the first focal area by the projection lens causes tissue processing in the second focal area in the eye. By imaging the focal area of the projection lens onto a focal area disposed downstream in the eye tissue by way of the lens-element system, different treatment depths in the eye can be achieved by the ophthalmological laser system without having to increase the focusing range of the ophthalmological laser system therefor. The ophthalmological patient interface apparatus facilitates a cost-effective alternative to large zoom lenses and, in particular, it is advantageous in that the application range of existing systems can be extended in a flexible and simple manner, without the existing system having to be replaced by new developments.

In an embodiment variant, the lens-element system comprises a relay optical unit which is configured to image the first focal area of the projection lens onto the second focal area in the eye.

In an embodiment variant, the lens-element system is configured to image a first image region on the first focal area of the projection lens onto a second image region, which is smaller than the first image region, on the second focal area in the eye.

In an embodiment variant, the lens-element system is configured to image the first focal area of the projection lens onto the second focal area in the eye lying in a region from the eye lens to the retina inclusive.

In an embodiment variant, the patient interface apparatus is developed in such a way that an interstice exists between the projection lens of the application head and the lens-element system in the state where the patient interface apparatus is coupled to the application head, said interstice containing a gas, a gas mixture or a vacuum, and that the first focal area of the projection lens comes to rest in the interstice.

In an embodiment variant, the lens-element system is configured to image the first focal area of the projection lens onto the second focal area in the eye in such a way that aberrations are corrected, said aberrations occurring on account of focusing the laser beam onto the first focal area in the interstice with a gas, a gas mixture or a vacuum instead of focusing the laser beam onto the first focal area in the eye tissue.

In an embodiment variant, the ophthalmological patient interface apparatus comprises optically identifiable reference markings which are arranged in the interstice.

In an embodiment variant, the patient interface apparatus is developed in such a way that the projection lens of the application head is mechanically freely displaceable over the lens-element system in the state where the patient interface apparatus is coupled to the application head.

In an embodiment variant, the ophthalmological patient interface apparatus comprises a fastening apparatus with one or more negative pressure chambers for fastening the patient interface apparatus to the eye, and the lens-element system is connected to the fastening apparatus in an interchangeable manner.

In an embodiment variant, the ophthalmological patient interface apparatus comprises a transparent protection barrier which is arranged between the eye and the lens-element system in the state where the patient interface apparatus is fastened to the eye.

In addition to the ophthalmological patient interface apparatus, the present invention moreover relates to an ophthalmological laser system which comprises an ophthalmological patient interface apparatus according to one of the aforementioned embodiment variants, a laser source for producing a laser beam, a projection lens for the focussed projection of the laser beam onto a focus on the first focal area and a scanning apparatus for moving the focus. The ophthalmological laser system moreover comprises a confocal detector which is coupled into the beam path between the laser source and the scanning apparatus and which is configured to capture a reflection of the laser beam by eye tissue lying in the second focal area.

In an embodiment variant, the ophthalmological laser system comprises a processor which is configured to control the ophthalmological laser system in such a way that the laser source is operated with reduced power which does not cause tissue processing and that the scanning apparatus moves the focus in the case of the reduced power in accordance with a defined scanning pattern, and to store values of the reflections captured by the confocal detector in a manner assigned to points of the scanning pattern.

In an embodiment variant, the ophthalmological laser system comprises an optical measuring system which is configured to optically ascertain a working region arranged on the second focal area along the beam path from the projection lens to the eye, wherein the optical measuring system comprises a camera configured to capture a plan view image of the working region and/or an OCT apparatus configured to ascertain the working region by optical coherence tomography.

In an embodiment variant, the ophthalmological laser system comprises an adaptation optical unit disposed upstream of the lens-element system of the ophthalmological patient interface apparatus in the beam path, said adaptation optical unit being configured to correct aberrations which occur during imaging of a focus of the laser beam from the first focal area to the second focal area, wherein the adaptation optical unit comprises one or more deformable mirrors, plates that are introducible into the beam path, LCD mirrors and/or lens-element systems.

In an embodiment variant, the ophthalmological laser system comprises an optical measuring system which is configured to optically capture a pupil of the eye, a processor which is configured to ascertain a pupil dimension and a beam expander apparatus disposed upstream of the lens-element system of the ophthalmological patient interface apparatus in the beam path, said beam expander apparatus being configured to adapt a beam width of the laser beam depending on the pupil dimension.

BRIEF DESCRIPTION OF THE DRAWINGS

An embodiment of the present invention is described below on the basis of an example. The exemplary embodiment is illustrated by the following attached figures.

WAYS OF IMPLEMENTING THE INVENTION

Figure 1:
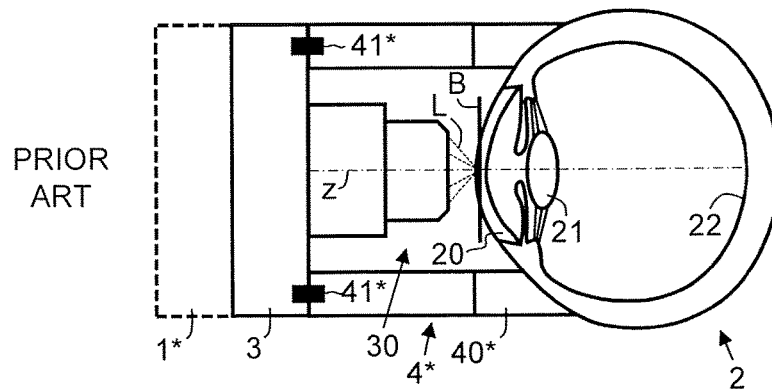
FIG. 1: schematically shows a cross section of an ophthalmological patient interface apparatus according to the prior art, which is fastened to an eye of a patient and mechanically coupled to an application head via a coupling apparatus.
Figure 2:
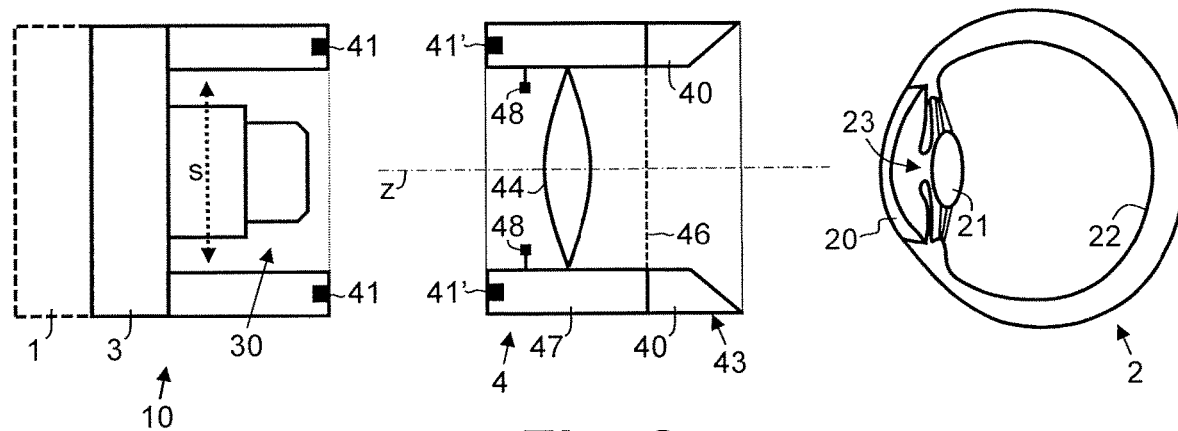
FIG. 2: schematically shows a cross section of an application head and an ophthalmological patient interface apparatus that is fastenable to an eye of a patient, said ophthalmological patient interface apparatus being mechanically coupleable to the application head and having a lens-element system.
Figure 3:
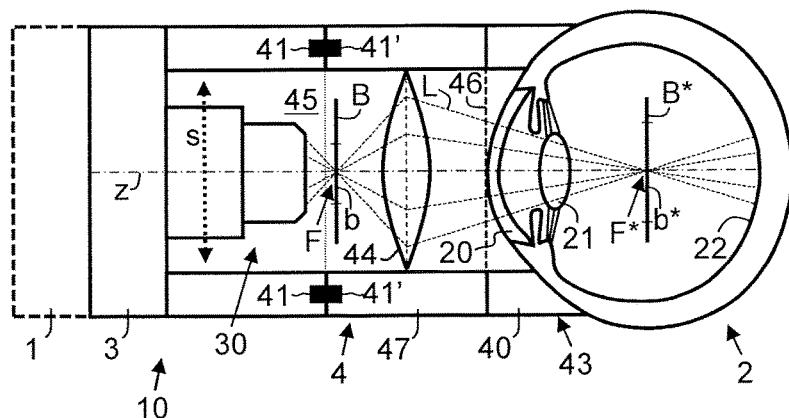
FIG. 3: schematically shows a cross section of an ophthalmological laser system having an application head and an ophthalmological patient interface apparatus that is fastened to an eye of a patient, said ophthalmological patient interface apparatus being mechanically coupled to the application head and having a lens-element system.
Figure 4:
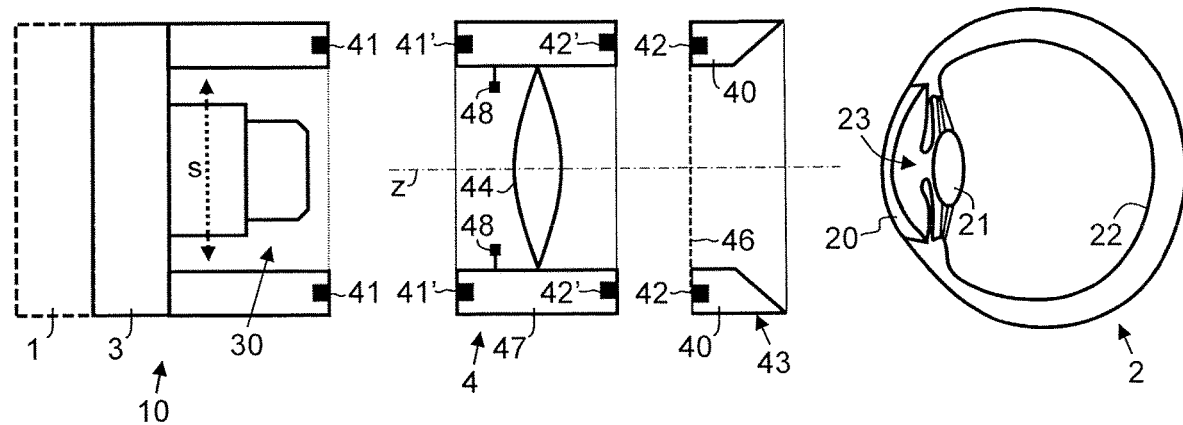
FIG. 4: schematically shows a cross section of an application head, an ophthalmological patient interface apparatus which is mechanically coupleable to the application head and which has a lens-element system, and a fastening apparatus which is mechanically coupleable to the ophthalmological patient interface apparatus, the patient interface apparatus being fastenable to the eye of a patient by way of said fastening apparatus.
Figure 5:
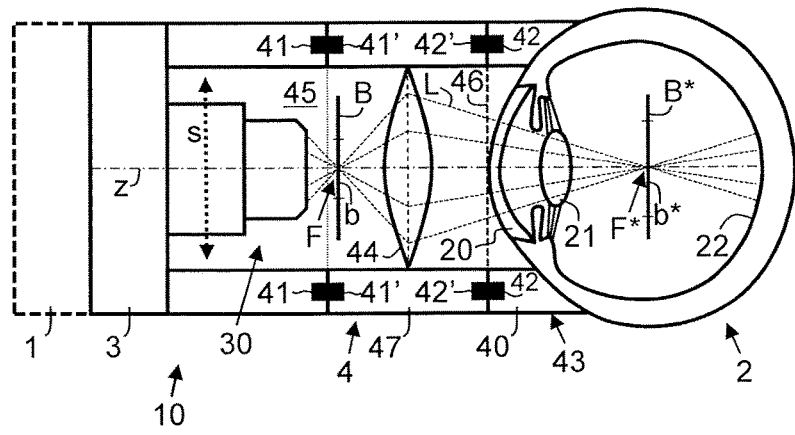
FIG. 5: schematically shows a cross section of an ophthalmological laser system with an application head and an ophthalmological patient interface apparatus which is mechanically coupled to the application head and which has a lens-element system, said ophthalmological patient interface apparatus being fastened in a mechanically coupled manner to a fastening apparatus at the eye of a patient.
Figure 6:
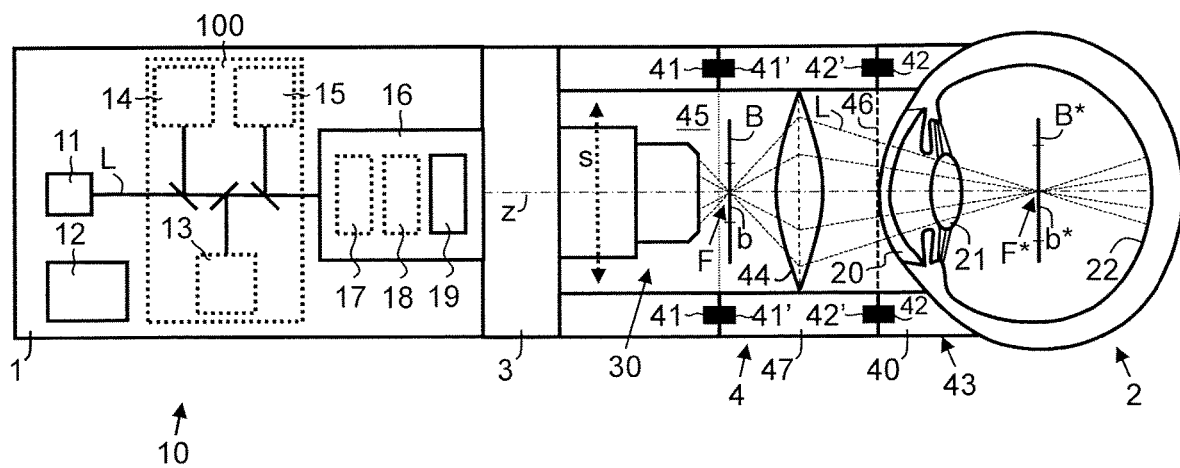
FIG. 6: schematically shows a cross section of an ophthalmological laser system with a laser apparatus, an application head and an ophthalmological patient interface apparatus which is mechanically coupled to the application head and which has a lens-element system, said ophthalmological patient interface apparatus being fastened in a mechanically coupled manner to a fastening apparatus at the eye of a patient, wherein a plurality of modules of the laser apparatus are illustrated by means of a block diagram.

In FIGS. 1 to 6, the reference sign 2 relates to an eye of a patient, with the cornea 20, the lens 21, the retina 22 and, in FIGS. 2 and 4, the pupil 23 respectively being provided with dedicated reference signs. In FIGS. 3, 5 and 6, the pupil is illustrated in a more widened state in comparison with FIGS. 1, 2 and 4; this is achieved, for example, by application of pupil-widening substances.

FIG. 1 schematically illustrates a cross section of an ophthalmological patient interface apparatus 4* according to the prior art, which, at one end, is mechanically coupled to an application head 3 of an ophthalmological laser apparatus 1* by way of a coupling apparatus 41* and which, at the other end, is fastened to the eye 2 by means of one or more negative pressure chambers 40*. During the treatment of the eye 2, the application head 3 is anchored to the eye 2 by means of the patient interface apparatus 4* and a laser beam L produced in the ophthalmological laser apparatus 1* is radiated from a projection lens 30 of the application head 3 onto a focal area B and into the eye 2, onto a focal area B of the projection lens 30 extending in the cornea 20 in the example of FIG. 1.

In FIGS. 2 to 6, the reference sign 10 relates to an ophthalmological laser system which comprises a laser apparatus 1 and an application head 3 with a projection lens 30. By way of example, the application head 3 is attached to the laser apparatus 1 by way of a stationary or movable support arm. In one embodiment variant, the projection lens 30 of the application head 3 is coupled to a drive and mechanically displaced in a scanning plane s (in x/y-directions) that extends perpendicular to the projection direction z, as indicated by the double-headed arrow s. It is clear from FIGS. 2-6 that the application head 3 has a coupling apparatus 41 which is configured to mechanically couple a patient interface apparatus 4 to the application head 3 and thereby fasten said patient interface apparatus to the application head 3. To this end, the patient interface apparatus 4 has a corresponding coupling apparatus 41'. By way of example, the coupling apparatuses 41, 41' are screwable to one another, engageable on one another, latchable on one another, coupled to one another by magnets or negative pressure (vacuum), or separably connected to one another in a mechanical fashion in a bayonet-cap-type manner.

In the state in which the patient interface apparatus 4 is coupled to the application head 3, an interstice 45 is formed between the projection lens 30 and the lens-element system 44. Depending on the embodiment variant, this interstice 45 contains a gas, a gas mixture, e.g. air, or a vacuum (seals, pumps and lines for producing a vacuum or filling a gas or gas mixture different to air are not illustrated in the figures). By coupling the patient interface apparatus 4 to the application head 3, the patient interface apparatus 4 is placed into a fixed position with respect to the ophthalmological laser system 10. As illustrated in FIGS. 2 and 4, the patient interface apparatus 4 has optically identifiable reference markings 48 which are arranged in the interstice 45, for example markings on transparent holders that are fastened to the lens-element support 47, which markings can be captured by an optical measuring system 100 and used by a processor 12 as geometrically known reference points.

In an embodiment variant, the patient interface apparatus 4 or the interstice 45 is developed in such a way that the projection lens 30 of the application head 3 is displaceable in a mechanically free manner in the scanning plane s in the interstice 45 above the lens-element system 44 in the state in which the patient interface apparatus 4 is coupled to the application head 3, as indicated by the double-headed arrow s.

As illustrated schematically in FIG. 6, the laser apparatus 1 comprises a plurality of components and functional modules, in particular a laser source 11 and an optical transfer system 16 for transferring a laser beam L produced in the laser source 11 from the laser source 11 to the projection lens 30. The laser source 11 is configured to produce a pulsed laser beam L, in particular femtosecond laser pulses. The optical transfer system 16 comprises a scanning apparatus 19 which is configured to deflect the laser beam L or the laser pulses thereof for the purposes of producing one or more scanning patterns. The scanning apparatus 19 comprises one or more deflectable deflection mirrors which are coupled to a drive, e.g. a piezo-drive or galvanic drive. The deflected laser beam L is focussed by the projection lens 30 onto a focal area B, where the focus F of the laser beam L is moved in an image region b according to the scanning pattern in accordance with the deflection by the scanning apparatus 19.

Depending on the embodiment variant, the optical transfer system 16 optionally comprises a beam expander apparatus 17 and/or an adaptation optical unit 18, the functions of which are described below.

Depending on the embodiment variant, the laser apparatus moreover optionally comprises an optical measuring system 100 having a confocal detector 13, a camera 14 and/or an OCT apparatus 15, the functions of which are likewise described below.

Moreover, one or more processors 12 or other programmed/configured electronic circuits are provided for controlling the laser apparatus 1 and the components and functional modules thereof.

In FIGS. 2 to 6, the reference sign 4 relates to an ophthalmological patient interface apparatus which comprises a lens-element support 47 with a lens-element system 44 attached thereto. As described above, the patient interface apparatus has a coupling apparatus 41' for mechanically coupling the patient interface apparatus 4 to the application head 3.

Moreover, the ophthalmological patient interface apparatus 4 comprises a fastening apparatus 43 for fastening the patient interface apparatus 4 to an eye 2 of a patient. By way of example, the fastening apparatus 43 is developed as a suction ring and comprises one or more negative pressure chambers 40 for anchoring the patient interface apparatus 4 to the eye 2 by negative pressure (vacuum pumps and suction lines are not illustrated in the figures).

In the embodiment variants of FIGS. 2 and 3, the fastening apparatus 43 is securely connected to the lens-element support 47 and the lens-element system 44 attached thereto. FIG. 2 shows the ophthalmological laser system 10 and the patient interface apparatus 4 in a manner separated from one another and detached from the eye 2. In FIG. 3, the patient interface apparatus 4 is illustrated mechanically coupled to the application head 3 of the ophthalmological laser system 10 and anchored to the eye by means of the fastening apparatus 43. In the embodiment variants of FIGS. 4 to 6, the fastening apparatus 43 and the lens-element support 47 with the lens-element system 44 attached thereto are separably connected to one another via coupling apparatuses 42, 42'. As illustrated schematically in FIGS. 4 to 6, the fastening apparatus 43 and the lens-element support 47 comprise appropriate coupling apparatuses 42, 42' to this end, the latter being developed as described above in conjunction with the coupling apparatuses 41, 41' for fastening the patient interface apparatus 4 to the application head 3. In one embodiment variant, the coupling apparatuses 42 of the fastening apparatus 43 are developed in accordance with the coupling apparatuses 41 of the application head 3 such that, when the lens-element support 47 and the lens-element system 44 are removed, the application head 3 can be coupled directly to the fastening apparatus 43 and thereby be directly connected to the fastening apparatus 43 and fastened to the eye 2. Particularly in this embodiment, the fastening apparatus 43 is provided as a disposable product which is disposed of after use on a patient, also for hygienic and medically preventative reasons. FIG. 4 shows the ophthalmological laser system 10 and the lens-element support 47 and the fastening apparatus 43 of the patient interface apparatus 4 in a manner separated from one another and detached from the eye 2. In FIGS. 5 and 6, the lens-element support 47 and the fastening apparatus 43 of the patient interface apparatus 4 are illustrated connected to one another, mechanically coupled to the application head 3 of the ophthalmological laser system 10 and anchored to the eye by means of the fastening apparatus 43.

FIGS. 3, 5 and 6 illustrate the beam path of the laser beam L from the projection lens 30 into the eye 2 in the case of the coupled lens-element system 44 of the patient interface apparatus 4. It is clear from FIGS. 3, 4 and 5 that the lens-element system 44 is disposed downstream of the projection lens 30 in the beam path, to be precise downstream of the focal area B of the projection lens 30, which lies in the interstice 45.

The lens-element system 44 comprises one or more optical lenses. In particular, the lens-element system 44 comprises a relay optical unit which is configured to image the focal area B of the projection lens 30 onto the focal area B* in the eye 2. Expressed differently, the laser beam L focussed by the projection lens 30 onto the focal area B (focus F), which expands again proceeding from the focus F downstream of the focal area B, is focussed onto the focal area B* (focus F*) by the lens-element system 44. When the laser source 11 is set to a power for tissue processing, tissue processing in the eye 2 is caused by imaging the focus F (on the focal area B of the projection lens 30) onto the focus F* (on the focal area B* in the eye 2). The relay optical unit is optimized in respect of imaging a first plane onto another second plane. Here, in particular, the relay optical unit is configured to image the first plane, in this case the focal area B, onto the other second plane, in this case the focal area B*, without aberrations or with aberrations that are as small as possible.

In an embodiment variant, the lens-element system 44 or the relay optical unit is configured to image an image region b on the focal area B of the projection lens 30 onto a comparatively smaller image region b* on the focal area B* in the eye 2. As a result, the spot (spot diameter d) formed by the focus F on the focal area B is imaged onto a comparatively smaller spot (spot diameter d*) of the focus F* on the focal area B* in the eye 2, as a result of which the local energy density in the focus F* on the focal area B* in the eye 2 is increased. This embodiment variant is advantageous, in particular, for the case where the laser system 10 is designed for surgery on the lens 21 and correspondingly has low focusing power (NA). This is because, in this case, using a correspondingly designed lens-element system 44 of the patient interface apparatus 4 facilitates the use of such a laser system 10 with an increased focusing power for treating the cornea 20.

In a further embodiment variant, the lens-element system 44 or the relay optical unit is configured to correct aberrations which arise in the case of "intermediate" focusing of the laser beam L onto the focal area B of the projection lens 30 because the focal area B, unlike in the arrangement according to FIG. 1, does not lie in the eye tissue, for example in the cornea 20, or in the liquid volume of a liquid-based patient interface, but instead lies outside of the eye 2 in the interstice 45 which contains a gas, a gas mixture or a vacuum.

In comparison with the arrangement according to the prior art illustrated in FIG. 1, the patient interface apparatus 4, which is coupled into the beam path between the projection lens 30 and the eye 2 and which has the lens-element system 44, facilitates an imaging or displacement of the focal area B, which, for example, comes to rest in the cornea 20 or in the anterior chamber of the eye 2 (the anterior chamber extends from the cornea 20 to the rear lens surface of the lens 21) using the arrangement according to the prior art, to the focal area B* in deeper-lying structures of the eye 2, in the region from and including the lens 21 to and including the retina 22, without having to undertake focus adjustments in the laser apparatus 1 or the projection lens 30 and without having to extend the focusing range of the laser apparatus 1 or of the projection lens 30 in the process. Thus, for example, a laser system 10 which is configured for anterior chamber surgery can be used for vitreous humour and retina surgery by interposing the patient interface apparatus 4. In one embodiment variant, the axial position (along the projection axis z) of the lens-element system 44 is adjustable by hand or by motor. In the latter case, the patient interface apparatus 4 comprises a movement driver for adjusting the lens-element system 44, said movement driver being actuatable by the processor 12 by way of e.g. an interface.

As illustrated schematically in FIGS. 2 to 6, the patient interface apparatus 4 comprises a transparent protection barrier 46 which protects the eye 2 from direct contact with the lens-element system 44 or contamination connected therewith. In the state where the patient interface apparatus 4 is fastened to the eye 2, the protection barrier 46 lies between the lens-element system 44 and the eye 2. The protection barrier 46 is a flexible film or membrane made of a plastic that is tolerated by the eye 2, a fixed glass disc or a curved contact body which, moreover, may also be configured to applanate the cornea 20.

The following paragraphs will discuss in more detail the processor 12 and the optional functional modules of the ophthalmological laser system 10 (optical transfer system 16, beam expander apparatus 17, adaptation optical unit 18, optical measuring system 100, confocal detector 13, camera 14 and OCT apparatus 15) connected therewith, said optional functional modules being illustrated schematically in FIG. 6 in a block diagram but also being able to be part of the laser apparatus 1 which is illustrated in FIGS. 2 to 5.

The optical measuring system 100 is configured to optically ascertain a working region b* arranged on the second focal area B* along the beam path from the projection lens 30 to the eye 2 by means of, depending on the embodiment variant, the confocal detector 13, the camera 14 and/or the OCT apparatus 15, wherein the measurement signals or measurement data of the optical measuring system 100 are received, stored and processed by the processor 12.

The optional confocal detector 13 is coupled into the beam path between the laser source 11 and the scanning apparatus 19 and configured to capture reflections of the laser beam L at eye tissue lying in the focal area B*. Expressed differently, the confocal detector 13 facilitates the detection of reflective eye structures if these lie in the focal area B*. For the purposes of testing or sizing a specific arrangement of the ophthalmological laser system 10 which has a coupled lens-element system 44 and which is anchored to the eye 2 by means of the fastening apparatus 43, a scanning pattern is passed over at reduced power, which does not cause tissue processing, and the reflections on the tissue are captured by way of the confocal detector 13. To this end, the processor 12 is configured to put the laser source 11 into a test mode with reduced power and to actuate the scanning apparatus 19 in such a way that the latter moves the focus F according to a test scanning pattern in the case of the reduced power. The processor 12 stores the reflection values in a manner assigned to the respectively relevant scanning points of the test scanning pattern, said reflection values being captured and supplied by the confocal detector 13 when the test scanning pattern is passed over. As a result, reflective tissue structures lying on the focal area B* can be captured. In combination with a focal adjustment of the projection lens 30 or a zoom apparatus of the laser apparatus 1 disposed downstream of the confocal detector 13, it is possible to capture the reflective tissue structures in multiple layers on focal areas B* of different depths and combine these to form a three-dimensional image or a 3D model of the eye structures. The confocal detector 13 offers the advantage of the target accuracy of the laser system 10 not being modified by an imprecise assembly of the apparatus (in particular of the application head 3 and patient interface apparatus 4) or by a (manual or motor-driven) displacement of the lens-element system 44, which can cause a displacement or a tilt of the image plane b*. By way of example, so-called floaters can be captured very accurately and can be reliably dissolved by laser pulses, even close to the retina 22 (without damaging the latter).

The camera 14, for example a CCD (charge-coupled device) camera, is configured to capture a plan view image of the working region b* on the focal area B*.

The OCT apparatus 15 is configured to capture the working region b* on the focal area B* and regions lying therebefore and therebehind by way of optical coherence tomography. Here, the additional optical path length between the working regions b and b* must be taken into account by adjusting a reference arm of the OCT apparatus 15.

In an embodiment variant, the optical measuring system 100, in particular the camera 14 or the OCT apparatus 15, is used to capture the pupil 23 of the eye. The processor 12 is configured to ascertain the current dimension of the pupil 23 from the image data or measurement data of the pupil 23 supplied by the optical measuring system 100. If the ascertained pupil dimension lies below a diameter threshold which would cause trimming of the beam width of the laser beam L, the processor 12 actuates the beam expander apparatus 17, disposed upstream of the lens-element system 44 in the beam path, so that said beam expander apparatus reduces the beam width of the laser beam L to such an extent that said laser beam no longer experiences trimming of the beam width by the pupil 23 in accordance with the ascertained pupil dimension.

The adaptation optical unit 18 is disposed upstream of the lens-element system 44 in the beam path and comprises one or more deformable mirrors, plates that are introducible into the beam path, LCD mirrors and/or lens-element systems. The adaptation optical unit 18 is configured to correct aberrations which may be caused when imaging a focus F of the laser beam L from the first focal area B onto the second focal area B* by means of the lens-element system 44. The adaptation optical unit is controlled by the processor 12, for example depending on wavefront errors when imaging the first focal area B onto the second focal area B*, said wavefront errors being captured during a calibration phase or being ascertained dynamically by way of a wavefront sensor (not illustrated here). In order to actively compensate aberrations caused by the apparatus assembly or the eye of the patient, the processor 12 controls the adaptation optical unit 18 using wavefront measurements which are captured with the aid of the wavefront sensor.

The invention claimed is:

1. Ophthalmological patient interface apparatus, comprising a coupling apparatus for mechanically coupling the patient interface apparatus to an application head of an ophthalmological laser system,
    wherein the patient interface apparatus comprises a lens-element system which is arranged between the eye and the application head in a state where the patient interface apparatus is coupled to the application head during treatment of an eye, said lens-element system being coupled into a beam path from a projection lens of the application head to the eye, wherein the lens-element system is configured in such a way that it images a first focal area of the projection lens, disposed upstream of the lens-element system in the beam path, onto a second focal area in the eye, disposed downstream of the lens-element system in the beam path, in such a way that a laser beam focused onto the first focal area by the projection lens causes tissue processing in the second focal area in the eye, and
    wherein the lens-element system comprises a relay optical unit which is configured to image the first focal area of the projection lens onto the second focal area in the eye.

2. Ophthalmological patient interface apparatus according to claim 1, wherein the patient interface comprises a fastening apparatus with one or more negative pressure chambers for fastening the patient interface apparatus to the eye, and the lens-element system is connected to the fastening apparatus in an interchangeable manner.

3. Ophthalmological patient interface apparatus according to claim 1, wherein the patient interface comprises a transparent protection barrier which is arranged between the eye and the lens-element system in the state where the patient interface apparatus is fastened to the eye.

4. Ophthalmological patient interface apparatus comprising a coupling apparatus for mechanically coupling the patient interface apparatus to an application head of an ophthalmological laser system, wherein the patient interface apparatus comprises a lens-element system which is arranged between the eye and the application head in a state where the patient interface apparatus is coupled to the application head during treatment of an eye, said lens-element system being coupled into a beam path from a projection lens of the application head to the eye, wherein the lens-element system is configured in such a way that it images a first focal area of the projection lens, disposed upstream of the lens-element system in the beam path, onto a second focal area in the eye, disposed downstream of the lens-element system in the beam path, in such a way that a laser beam focused onto the first focal area by the projection lens causes tissue processing in the second focal area in the eye, and
    wherein the patient interface apparatus is configured such that an interstice exists between the projection lens of the application head and the lens-element system in the state where the patient interface apparatus is coupled to the application head, said interstice containing a gas, a gas mixture or a vacuum, and that the first focal area of the projection lens comes to rest in the interstice.

5. Ophthalmological patient interface apparatus according to claim 4, wherein the lens-element system is configured to image the first focal area of the projection lens onto the second focal area in the eye in such a way that aberrations are corrected, said aberrations occurring on account of focusing the laser beam onto the first focal area in the interstice with a gas, a gas mixture or a vacuum instead of focusing the laser beam onto the first focal area in the eye tissue.

6. Ophthalmological patient interface apparatus according to claim 4, wherein the patient interface comprises optically identifiable reference markings which are arranged in the interstice.

7. Ophthalmological laser system, comprising an ophthalmological interface apparatus according to claim 1, wherein the ophthalmological patient interface apparatus comprises a coupling apparatus for mechanically coupling the patient interface apparatus to an application head of the ophthalmological laser system, a lens-element system which is arranged between the eye and the application head in a state where the patient interface apparatus is coupled to the application head during treatment of an eye, said lens-element system being coupled into a beam path from a projection lens of the application head to the eye, wherein the lens-element system is configured in such a way that it images a first focal area of the projection lens, disposed upstream of the lens-element system in the beam path, onto a second focal area in the eye, disposed downstream of the lens-element system in the beam path, in such a way that a laser beam focused onto the first focal area by the projection lens causes tissue processing in the second focal area in the eye, and wherein the ophthalmological laser system further comprises a laser source for producing a laser beam, a projection lens for the focused projection of the laser beam onto a focus on the first focal area, a scanning apparatus for moving the focus, wherein the ophthalmological laser system moreover comprises a confocal detector which is coupled into the beam path between the laser source and the scanning apparatus and which is configured to capture a reflection of the laser beam by eye tissue lying in the second focal area.

8. Ophthalmological laser system according to claim 7, wherein the laser system comprises a processor which is configured to control the ophthalmological laser system in such a way that the laser source is operated with reduced power which does not cause tissue processing and that the scanning apparatus moves the focus in the case of the reduced power in accordance with a defined scanning pattern, and to store values of the reflections captured by the confocal detector in a manner assigned to points of the scanning pattern.

9. Ophthalmological laser system according to claim 7, wherein the laser system comprises an optical measuring system which is configured to optically ascertain a working region arranged on the second focal area along the beam path, from the projection lens to the eye, wherein the optical measuring system comprises at least one of: a camera configured to capture a plan view image of the working region and an OCT apparatus configured to ascertain the working region by optical coherence tomography.

10. Ophthalmological laser system according to claim 7, wherein the laser system comprises an adaptation optical unit disposed upstream of the lens-element system of the ophthalmological patient interface apparatus in the beam path, said adaptation optical unit being configured to correct aberrations which occur during imaging of a focus of the laser beam from the first focal area to the second focal area, wherein the adaptation optical unit comprises at least one of: a deformable mirror, a plate that is introducible into the beam path, an LCD mirror and a lens-element system.

11. Ophthalmological laser system according to claim 7, wherein the laser system comprises an optical measuring system which is configured to optically capture a pupil of the eye, a processor which is configured to ascertain a pupil dimension and a beam expander apparatus disposed upstream of the lens-element system of the ophthalmological patient interface apparatus in the beam path, said beam expander apparatus being configured to adapt a beam width of the laser beam depending on the pupil dimension.

12. The ophthalmological laser system of claim 7, wherein the lens-element system is configured to image a first image region, on the first focal area of the projection lens, onto a second image region, which is smaller than the first image region, on the second focal area in the eye.

13. The ophthalmological laser system of claim 7, wherein the lens-element system is configured to image the first focal area of the projection lens onto the second focal area in the eye lying in a region from the eye lens inclusive to the retina inclusive.

14. The ophthalmological laser system of claim 7, wherein the patient interface apparatus is configured such that an interstice exists between the projection lens of the application head and the lens-element system in the state where the patient interface apparatus is coupled to the application head, said interstice containing a gas, a gas mixture or a vacuum, and that the first focal area of the projection lens comes to rest in the interstice.

15. The ophthalmological laser system of claim 14, wherein the lens-element system is configured to image the first focal area of the projection lens onto the second focal area in the eye in such a way that aberrations are corrected, said aberrations occurring on account of focusing the laser beam onto the first focal area in the interstice with a gas, a gas mixture or a vacuum instead of focusing the laser beam onto the first focal area in the eye tissue.

16. The ophthalmological laser system of claim 7, wherein the patient interface apparatus is configured such that the projection lens of the application head is mechanically freely displaceable over the lens-element system in the state where the patient interface apparatus is coupled to the application head.

17. The ophthalmological laser system of claim 7, wherein the patient interface comprises a fastening apparatus with one or more negative pressure chambers for fastening the patient interface apparatus to the eye, and the lens-element system is connected to the fastening apparatus in an interchangeable manner.

18. Ophthalmological patient interface apparatus comprising a coupling apparatus for mechanically coupling the patient interface apparatus to an application head of an ophthalmological laser system, wherein the patient interface apparatus comprises a lens-element system which is arranged between the eye and the application head in a state where the patient interface apparatus is coupled to the application head during treatment of an eye, said lens-element system being coupled into a beam path from a projection lens of the application head to the eye, wherein the lens-element system is configured in such a way that it images a first focal area of the projection lens, disposed upstream of the lens-element system in the beam path, onto a second focal area in the eye, disposed downstream of the lens-element system in the beam path, in such a way that a laser beam focused onto the first focal area by the projection lens causes tissue processing in the second focal area in the eye, and wherein the lens-element system is configured to image a first image region, on the first focal area of the projection lens, onto a second image region, which is smaller than the first image region, on the second focal area in the eye.

19. Ophthalmological patient interface apparatus comprising a coupling apparatus for mechanically coupling the patient interface apparatus to an application head of an ophthalmological laser system, wherein the patient interface apparatus comprises a lens-element system which is arranged between the eye and the application head in a state where the patient interface apparatus is coupled to the application head during treatment of an eye, said lens-element system being coupled into a beam path from a projection lens of the application head to the eye, wherein the lens-element system is configured in such a way that it images a first focal area of the projection lens, disposed upstream of the lens-element system in the beam path, onto a second focal area in the eye, disposed downstream of the lens-element system in the beam path, in such a way that a laser beam focused onto the first focal area by the projection lens causes tissue processing in the second focal area in the eye, and wherein the lens-element system is configured to image the first focal area of the projection lens onto the second focal area in the eye lying in a region from the eye lens inclusive to the retina inclusive.

20. Ophthalmological patient interface apparatus comprising a coupling apparatus for mechanically coupling the patient interface apparatus to an application head of an ophthalmological laser system, wherein the patient interface apparatus comprises a lens-element system which is arranged between the eye and the application head in a state where the patient interface apparatus is coupled to the application head during treatment of an eye, said lens-element system being coupled into a beam path from a projection lens of the application head to the eye, wherein the lens-element system is configured in such a way that it images a first focal area of the projection lens, disposed upstream of the lens-element system in the beam path, onto a second focal area in the eye, disposed downstream of the lens-element system in the beam path, in such a way that a laser beam focused onto the first focal area by the projection lens causes tissue processing in the second focal area in the eye, and wherein the patient interface apparatus is configured such that the projection lens of the application head is mechanically freely displaceable over the lens-element system in the state where the patient interface apparatus is coupled to the application head.

* * * * *